United States Patent
Nakagawa et al.

[11] Patent Number: 5,866,631
[45] Date of Patent: Feb. 2, 1999

[54] DENTAL PRIMER COMPOSITION AND POLYMERIZATION CATALYST

[75] Inventors: Hiroyuki Nakagawa; Hideki Ohno, both of Tokuyama, Japan

[73] Assignee: Tokuyama Corporation, Yamaguchi, Japan

[21] Appl. No.: 894,596

[22] PCT Filed: Dec. 20, 1996

[86] PCT No.: PCT/JP96/03739

§ 371 Date: Aug. 22, 1997

§ 102(e) Date: Aug. 22, 1997

[87] PCT Pub. No.: WO97/23191

PCT Pub. Date: Jul. 3, 1997

[30] Foreign Application Priority Data

Dec. 22, 1995 [JP] Japan ................................. 7-335546

[51] Int. Cl.$^6$ ................................. C08K 5/55; A61K 6/00
[52] U.S. Cl. ........................... 523/118; 522/29; 524/183; 524/184; 524/413; 526/196; 526/198
[58] Field of Search ..................... 523/118; 526/196, 526/198; 522/29; 524/183, 184, 413

[56] References Cited

U.S. PATENT DOCUMENTS

| | | |
|---|---|---|
| 4,937,159 | 6/1990 | Gottschalk et al. . |
| 4,977,511 | 12/1990 | Gottschalk et al. . |
| 5,066,741 | 11/1991 | Campbell, Jr. . |
| 5,124,235 | 6/1992 | Fukui et al. ............................. 522/29 |
| 5,369,178 | 11/1994 | Miyazaki et al. . |
| 5,530,038 | 6/1996 | Yamamoto et al. . |
| 5,539,070 | 7/1996 | Zharov et al. ........................... 526/198 |
| 5,587,406 | 12/1996 | Yamamoto et al. . |
| 5,670,559 | 9/1997 | Zeng et al. .............................. 523/118 |

FOREIGN PATENT DOCUMENTS

| | | |
|---|---|---|
| 0339841 | 11/1989 | European Pat. Off. . |
| 339841A2 | 11/1989 | European Pat. Off. . |
| 0421659 | 4/1991 | European Pat. Off. . |
| 421659A2 | 4/1991 | European Pat. Off. . |
| 0522456 | 1/1993 | European Pat. Off. . |
| 522456A2 | 1/1993 | European Pat. Off. . |
| 3240712 | 10/1991 | Japan . |
| 48368 | 1/1992 | Japan . |
| 6192029 | 7/1994 | Japan . |
| 6192030 | 7/1994 | Japan . |
| WO 94/29356A1 | 12/1994 | Japan . |
| 089820 | 4/1995 | Japan . |
| 782115 | 4/1995 | Japan . |
| 797306 | 4/1995 | Japan . |
| 9429356 | 12/1994 | WIPO . |

*Primary Examiner*—Andrew E.C. Merriam
*Attorney, Agent, or Firm*—Birch, Stewart, Kolasch & Birch, LLP

[57] ABSTRACT

There is provided a dental primer composition capable of obtaining high adhesive strength to both dentin and enamel, as a pretreatment material for a chemically polymerizable adhesive. This composition is a dental primer composition comprising a polymerizable monomer containing an acidic group, water, aryl borate and transition metal compound.

19 Claims, No Drawings

DENTAL PRIMER COMPOSITION AND POLYMERIZATION CATALYST

[TECHNICAL FIELD OF THE INVENTION]

This invention relates to a dental primer composition and a polymerization catalyst. More specifically, it relates to a dental primer composition for firmly bonding a crown repairing material such as a composite resin, metal or ceramic to a tooth in a dental treatment field and to a polymerization catalyst useful particularly for this purpose.

[BACKGROUND OF TECHNIQUE]

To repair a tooth damaged by dental caries or by accident, a crown repair material such as a composite resin, metal, ceramic or the like is bonded to the tooth by an adhesive. As the adhesive for bonding a crown repair material to the tooth, there are currently available optically polymerizable adhesives and chemically polymerizable adhesives which are used depending on the type of a crown material. For example, an optically curable bonding material is used for repairing by using optically curable composite resins, while a resin cement which is a chemically polymerizable adhesive is used for repairing by using metal casts and ceramics.

The adhesive is required to keep the crown repair material firmly bonded to the tooth for a long time in such a severe environment as the oral cavity. If the adhesive strength of the adhesive is low or the durability of the adhesive is insufficient, the repair material may fall off, or a gap may be produced between the tooth and the repair material with the result that bacteria may enter the gap, causing secondary dental caries.

The hard tissue of a tooth consists of enamel and dentin and a crown repair material is required to be bonded to both enamel and dentin clinically. Heretofore, to improve adhesion, the surface of a tooth has been pretreated prior to the application of an adhesive. A material for this pretreatment is generally an acidic aqueous solution for demineralizing the surface of a tooth, such as an aqueous solution of phosphoric acid, maleic acid or citric acid. In the case of enamel, the adhesion mechanism to the treated surface is mechanical macroscopic retention produced when an adhesive permeates the surface that has been made rough by demineralizing with an acidic aqueous solution, and hardens. Thereby, sufficient adhesive strength is obtained clinically. On the other hand, in the case of dentin, the adhesion mechanism is mechanical microscopic retention produced when an adhesive infiltrates into micro voids of a sponge-like collagen fiber exposed to the surface of a tooth after demineralizing, and hardens. However, since the infiltration of the adhesive into the exposed collagen layer is not easy, a generally called primer which is a permeation accelerating material is used and hence, operation becomes complicated.

To cope with this problem, for the purpose of simplifying bonding operation, a primer for the simultaneous pretreatment of both enamel and dentin has been studied. Japanese Laid-open Patent Publication Hei 3-240712 discloses a primer composition comprising a polymerizable monomer containing an acidic group, a polymerizable monomer containing a hydroxyl group, water and a curing material; Japanese Laid-open Patent Publication Hei 4-8368 a primer composition comprising a polymerizable monomer containing an acidic group, a polymerizable monomer containing a hydroxyl group, water and an amino compound having an acid group; Japanese Laid-open Patent Publication Hei 6-192029 discloses a pretreatment material comprising vinyl phosphonic acid, vinyl phosphonic acid metal salt, carboxylic acid having a hydrophobic group, water and alcohol; Japanese Laid-open Patent Publication Hei 6-192030 a pretreatment material comprising an organic sulfonic acid metal salt, organic carboxylic acid having a hydrophobic group, water and alcohol; Japanese Laid-open Patent Publication Hei 7-82115 a primer composition comprising a vinyl compound having an acidic group, a vinyl compound having a hydroxyl group, water, aromatic sulfinic acid and amine; Japanese Laid-open Patent Publication Hei 7-89820 a primer composition comprising a polymerizable monomer having an acidic group, water and a compound having an amide group and a hydroxyl group in the molecule; and Japanese Laid-open Patent Publication Hei 7-97306 a primer comprising a polymerizable monomer having an acidic group, an organic solvent and water as well as an adhesive system in which a curable composition comprising a polymerizable monomer having an acidic group, a polymerizable monomer having a hydroxyl group and a polymerization initiator are used.

However, when an optically curable adhesive such as a bonding material for composite resins or the like is used, all of the above compositions have adhesive force to both enamel and dentin. However, when a chemically polymerizable adhesive such as resin cement or the like is used, the compositions cannot necessarily have sufficient adhesive force yet. Chemically polymerizable adhesives generally have a lower rate of polymerization than optically polymerizable adhesives and hence, are inferior in adhesive strength. When trialkyl boron (or partial oxide thereof) which has high catalytic activity among the chemically polymerizable adhesives is used, high adhesive strength can be obtained, but it is necessary to separately keep the catalyst from a polymerizable compound before use because the catalyst is chemically unstable. Or rather, therefore, it involves a drawback that operation becomes complicated.

To cope with this problem, not only when an optically polymerizable adhesive is used but also when a chemically polymerizable adhesive is used, the development of a pretreatment material which can gain excellent adhesive strength has been desired.

[DISCLOSURE OF THE INVENTION]

It is an object of the present invention to provide a novel dental primer composition.

It is another object of the present invention to provide a primer composition with which high adhesive strength to both dentin and enamel can be obtained by a single operation when it is applied to the surface of tooth irrespective of a chemically polymerizable adhesive or an optically polymerizable adhesive.

It is a further object of the present invention to provide a novel polymerization catalyst, particularly a polymerization catalyst advantageously used for a polymerizable monomer or a composition containing the same, such as a dental primer composition; and a catalyst component thereof.

Other objects and advantages of the present invention will become apparent from the following description.

The inventors of the present invention have conducted intensive studies to attain the above objects and advantages, and have found that when an aryl borate and a transition metal compound are used as polymerization catalyst components for a dental primer composition, the dental primer composition provides high adhesive strength to both enamel and dentin not only when an optically polymerizable adhesive is used but also when a chemically polymerizable adhesive is used. This finding has led to the present invention.

That is, the above objects and advantages of the present invention can be firstly attained by a dental primer composition comprising (A) a polymerizable monomer containing an acidic group, (B) water, (C) an aryl borate and (D) a transition metal compound.

The polymerizable monomer containing an acidic group (A) used in the dental primer composition or dental primer of the present invention contains at least one acidic group such as carboxylic acid group, phosphoric acid group, sulfonic acid group or phosphonic acid group in one molecule. The polymerizable monomer preferably contains, as a polymerizable group, at least one radical polymerizable unsaturated group such as acryloyl group, methacryloyl group, styryl group, vinyl group or allyl group in one molecule.

The polymerizable monomer containing a carboxylic acid group out of the above polymerizable monomers containing an acidic group preferably includes a monocarboxylic acid, dicarboxylic acid, tricarboxylic acid or tetracarboxylic acid. Examples thereof are (meth)acrylic acid, maleic acid, p-vinylbenzoic acid, 11-(meth)acryloyloxy-1,1-undecanedicarboxylic acid, 2-methacryloyloxyethyl 3'-methacryloyloxy-2'(3,4-dicarboxybenzoyloxy)propyl succinate (MTS), 2-methacryloyloxyethyl hydrogen malate, 1,4-di(meth)acryloyloxymethylpyromellitic acid, 6-(meth) acryloyloxyethylnaphthalene-1,2,6-tricarboxylic acid, 4-(meth)acryloyloxymethyltrimellitic acid and an anhydride thereof, 4-(meth)acryloyloxyethyltrimellitic acid, 4-(meth) acryloyloxybutyltrimellitic acid and an anhydride thereof, 4-[2-hydroxy-3-(meth)acryloyloxy]butyltrimellitic acid and an anhydride thereof, 2,3-bis(3,4-dicarboxybenzoyloxy) propyl (meth)acrylate, N,O-di(meth)acryloyloxytyrosine, O-(meth)acryloyloxytyrosine, N-(meth)acryloyloxytyrosine, N-(meth)acryloyl-p-aminobenzoic acid, N-(meth)acryloyl, O-aminobenzoic acid, N-(meth) acryloyl 5-aminosalicylic acid, N-(meth)acryloyl 4-aminosalicylic acid, 2-, 3- or 4-(meth)acryloyloxybenzoic acid, addition product of 2-hydroxyethyl (meth)acrylate and pyromellitic dianhydride, 2-(3,4-dicarboxybenzoyloxy)-1,3-di(meth)acryloyloxypropane, 4-[(2-hydroxy-3-(meth) acryloyloxypropyl)amino]phthalic acid, 3 or 4-[N-methyl-N-(2-hydroxy-3-(meth)acryloyloxypropyl)amino]-phthalic acid and the like. Out of these, the preferred are dicarboxylic acids and the more preferred are 11-methacryloyloxy-1,1-undecanedicarboxylic acid (MAC-10), 2-methacryloyloxyethyl 3'-methacryloyloxy-2'(3,4-dicarboxybenzoyloxy)propyl succinate (MTS), 4-methacryloyloxyethyltrimellitic anhydride (4-META), 4-acryloyloxyethyltrimellitic acid (4-AET), and the like.

Examples of the polymerizable monomer containing a phosphoric acid group include 2-(meth)acryloyloxyethyl dihydrogen phosphate, 2-(meth)acryloyloxyethyl acid phosphate, 2 or 3-(meth)acryloyloxypropyl acid phosphate, 4-(meth)acryloylbutyl acid phosphate, 6-(meth) acryloyloxybutyl acid phosphate, 8-(meth)acryloyloxydecyl acid phosphate, 10-(meth)acryloyloxydecyl acid phosphate, 12-(meth)acryloyloxydodecyl acid phosphate, bis[2-(meth) acryloyloxyethyl]acid phosphate, bis[2-(meth) acryloyloxyethyl]hydrogen phosphate, 2-(meth) acryloyloxyethylphenyl acid phosphate (phenyl-P), 2 -(meth)acryloyloxyethyl-p-ethoxyphenyl acid phosphate, and the like. Compounds obtained by substituting a thiophosphoric acid group for the phosphoric acid group of these compounds are also included. Out of these compounds, 2-methacryloxyethyl dihydrogen phosphate, 2-(meth) acryloyloxyethylphenyl acid phosphate and the like are preferred.

Further, examples of the polymerizable monomer containing a sulfonic acid group include 2-sulfoethyl (meth) acrylate, 2-methyl-2-(meth)acrylamidepropanesulfonic acid, 2 or 1-sulfo-1 or 2-propyl (meth)acrylate, 1 or 3-sulfo-2-butyl (meth)acrylate, 3-bromo-2-sulfo-2-propyl (meth) acrylate, 3-methoxy-1-sulfo-2-propyl (meth)acrylate, 1,1-dimethyl-2-sulfoethyl (meth)acrylamide, 3-methoxy-1-sulfo-2-propyl (meth)acrylate, and the like. Out of these, 2-methy- 2-(meth)acrylamidepropanesulfonic acid is preferred.

A typical example of phosphonic acid is vinyl phosphonic acid.

These polymerizable monomers containing an acidic group may be used in combination of plural monomers as required.

Out of the above polymerizable monomers containing an acidic group, polymerizable monomers containing a carboxylic acid group and polymerizable monomers containing a phosphoric acid group are preferred because they are excellent in adhesion to tooth. A use in combination of these monomers is more preferred.

Water as the component (B) contained in the dental primer of the present invention is used to demineralize the tooth and preferably contains substantially no impurities which impair storage stability, bio adaptability and adhesion. Demineralized water and distilled water are advantageously used as the water.

The aryl borate as the component (C) contained in the dental primer composition of the present invention has in one molecular at least one aryl group and boron which are directly bonded to each other and is preferably represented by the following general formula (1):

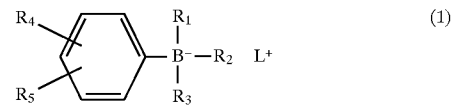

wherein $R_1$, $R_2$ and $R_3$ are the same or different and each an alkyl group, alkenyl group, alkinyl group, aryl group, aralkyl group or alkaryl group and may be substituted, $R_4$ and $R_5$ are the same or different and each a hydrogen atom, halogen atom, alkyl group which may be substituted or aryl group which may be substituted, and $L^+$ is a metal ion, quaternary ammonium salt, quaternary pyridinium salt, quaternary quinolinium ion or phosphonium ion.

Since aryl borates having no boron-aryl bond are extremely unstable in shelf life storage and easily decompose by reacting with oxygen contained in air, they cannot be used as a surface treatment agent for the tooth.

Specific examples of the aryl borate suitably usable include aryl borates having one aryl group in one molecule, such as sodium salts, lithium salts, potassium salts, magnesium salts, tetrabutyl ammonium salts, tetramethyl ammonium salts, tetraethyl ammonium salts, methylpyridinium salts, ethylpyridinium salts, butylpyridinium salts, methylquinolinium salts, ethylquinolinium salts and butylquinolinium salts of trialkylphenylboron, trialkyl(p-chlorophenyl) boron, trialkyl(p-fluorophenyl)boron, trialkyl(p-methoxyphenyl)boron, trialkyl(m-methoxyphenyl)boron, trialkyl(p-ethoxyphenyl)boron, trialkyl(m-ethoxyphenyl) boron, trialkyl(p-butoxyphenyl)boron, trialkyl(m-butoxyphenyl)boron, trialkyl(p-methylphenyl)boron, trialkyl(m-methylphenyl)boron, trialkyl(p-ethylphenyl) boron, trialkyl(m-ethylphenyl)boron, trialkyl(p-butylphenyl)boron, trialkyl(m-butylphenyl)boron, trialkyl (3,5-bistrifluoromethyl)phenylboron and trialkyl[3,5-bis(1, 1,1,3,3,3-hexafluoro-2-methoxy-2-propyl)phenyl]boron (hereinabove, the alkyl group is n-butyl, n-octyl, n-dodecyl or the like).

Examples of the aryl borate having two aryl groups in one molecule include sodium salts, lithium salts, potassium salts, magnesium salts, tetrabutyl ammonium salts, tetramethyl ammonium salts, tetraethyl ammonium salts, methylpyridinium salts, ethylpyridinium salts, butylpyridinium salts, methylquinolinium salts, ethylquinolinium salts and butylquinolinium salts of dialkyldiphenylboron, dialkyldi(p-chlorophenyl)boron, dialkyldi(p-fluorophenyl)boron, dialkyldi(p-methoxyphenyl)boron, dialkyldi(m-methoxyphenyl)boron, dialkyldi(p-ethoxyphenyl)boron, dialkyldi(m-ethoxyphenyl)boron, dialkyldi(p-butoxyphenyl)boron, dialkyldi(m-butoxyphenyl)boron, dialkyldi(p-methylphenyl)boron, dialkyldi(m-methylphenyl)boron, dialkyldi(p-ethylphenyl)boron, dialkyldi(m-ethylphenyl)boron, dialkyldi(p-butylphenyl)boron, dialkyldi(m-butylphenyl)boron, dialkyldi(3,5-bistrifluoromethyl)phenylboron and dialkyldi[3,5-bis(1,1,1,3,3,3-hexafluoro-2-methoxy-2-propyl)phenyl]boron (hereinabove, alkyl group is n-butyl, n-ocyl, n-dodecyl or the like).

Examples of the aryl borate having three aryl groups in one molecule include sodium salts, lithium salts, potassium salts, magnesium salts, tetrabutyl ammonium salts, tetramethyl ammonium salts, tetraethyl ammonium salts, methylpyridinium salts, ethylpyridinium salts, butylpyridinium salts, methylquinolinium salts, ethylquinolinium salts and butylquinolinium salts of monoalkyltriphenylboron, monoalkyltri(p-chlorophenyl)boron, monoalkyltri(p-fluorophenyl)boron, monoalkyltri(p-methoxyphenyl)boron, monoalkyltri(m-methoxyphenyl)boron, monoalkyltri(p-ethoxyphenyl)boron, monoalkyltri(m-ethoxyphenyl)boron, monoalkyltri(p-butoxyphenyl)boron, monoalkyltri(m-butoxyphenyl)boron, monoalkyltri(p-methylphenyl)boron, monoalkyltri(m-methylphenyl)boron, monoalkyltri(p-ethylphenyl)boron, monoalkyltri(m-ethylphenyl)boron, monoalkyltri(p-butylphenyl)boron, monoalkyltri(m-butylphenyl)boron, monoalkyltri(3,5-bistrifluoromethyl)phenylboron and monoalkyltri[3,5-bis(1,1,1,3,3,3-hexafluoro-2-methoxy-2-propyl)phenyl]boron (hereinabove, alkyl group is n-butyl, n-ocyl, n-dodecyl or the like).

Examples of the aryl borate having four aryl groups in one molecule include sodium salts, lithium salts, potassium salts, magnesium salts, tetrabutyl ammonium salts, tetramethyl ammonium salts, tetraethyl ammonium salts, methylpyridinium salts, ethylpyridinium salts, butylpyridinium salts, methylquinolinium salts, ethylquinolinium salts and butylquinolinium salts of tetraphenylboron, tetranaphthylboron, tetrabiphenylboron, tetrakis(p-chlorophenyl)boron, tetrakis(p-fluorophenyl)boron, tetrakis(p-methoxyphenyl)boron, tetrakis(m-methoxyphenyl)boron, tetrakis(p-ethoxyphenyl)boron, tetrakis(m-ethoxyphenyl)boron, tetrakis(p-butoxyphenyl)boron, tetrakis(m-butoxyphenyl)boron, tetrakis(p-methylphenyl)boron, tetrakis(m-methylphenyl)boron, tetrakis(p-ethylphenyl)boron, tetrakis(m-ethylphenyl)boron, trialkyl(p-butylphenyl)boron, tetrakis(m-butylphenyl)boron, tetrakis(3,5-bistrifluoromethyl)phenylboron and tetrakis[3,5-bis(1,1,1,3,3,3-hexafluoro-2-methoxy-2-propyl)phenyl]boron (hereinabove, alkyl group is n-butyl, n-ocyl, n-dodecyl, n-dodecyl or the like).

The above aryl borates may be used alone or in admixture of two or more.

Known transition metal compounds may be used as the component (D) contained in the dental primer of the present invention. Specific examples of the transition metal compound include bromides such as vanadium bromide, nickel bromide, copper bromide, iron bromide and cobalt bromide; chlorides such as nickel chloride, vanadium chloride, palladium chloride, nickel chloride, titanocene dichloride, titanium chloride, iron chloride and cobalt chloride; fluorides, such as vanadium fluoride, cobalt fluoride, copper fluoride, nickel fluoride and potassium titanium fluoride; sulfates such as palladium sulfate, nickel sulfate, titanium sulfate, copper sulfate, iron sulfate and cobalt sulfate; nitrates such as nickel nitrate, palladium nitrate, nickel nitrate, iron nitrate and cobalt nitrate; inorganic acid salts such as phosphates exemplified by iron diphosphate and cobalt phosphate; organic acid salts such as nickel acetate, copper acetate, cobalt acetate, cobalt benzoate, copper citrate, iron citrate, potassium titanium oxalate, iron oxalate, cobalt oxalate, iron lactate, iron fumarate, copper acrylate, copper methacrylate, nickel sulfaminate, vanadium oxide stearate, cobalt stearate, vanadium naphthenate, cobalt naphthenate and cobalt gluconate; hydroxides such as palladium hydroxide, nickel hydroxide, iron hydroxide, copper hydroxide and cobalt hydroxide; and organic complexes with acetylacetone such as vanadium acetyl acetonate, nickel acetylacetonato, copper acetylacetonato, iron acetylacetonato and cobalt acetylacetonato or with EDTA. Transition metals contained in these transition metal compounds may have any valence. Out of these transition metal compounds, iron, cobalt and copper compounds are preferred and iron and copper compounds are particularly preferred. The transition metal compounds may be used alone or in combination.

The primer composition of the present invention comprising the above components (A), (B), (C) and (D) preferably comprises 5 to 55% by weight of the polymerizable monomer containing an acidic group (A), 0.1 to 20% by weight of the aryl borate (C), 0.0001 to 20% by weight of the transition metal compound (D) and the remainder which is water (B), based on the total weight of these components.

When the polymerizable monomer containing an acidic group (A) is used in a proportion of from 5 to 55% by weight, the primer composition exhibits excellent adhesive force to the tooth, while the polymerizable monomer containing an acidic group (A) is preferably used in a proportion of from 5 to 25% by weight. When the proportion is less than 5% by weight, adhesive force to the enamel is liable to reduce and when it is more than 25% by weight, the adhesive strength to the dentin is liable to lower.

The proportion of the aryl borate (C) is preferably 0.1 to 20% by weight, more preferably 0.2 to 15% by weight, the most preferably 0.5 to 10% by weight.

The proportion of the transition metal compound (D) is preferably 0.0001 to 20% by weight, more preferably 0.02 to 10% by weight, particularly preferably 0.1 to 5% by weight. When the proportion is less than 0.0001% by weight, the effect is small, while when it is more than 20% by weight, the adhesive strength lowers.

The proportion of water (B) is the remainder of the total which is 100% by weight. That is, since the proportion of water changes according to the proportions of other components, it is not particularly limited. To demineralize the enamel and obtain mechanical retention, water is preferably contained in a proportion of not less than 5% by weight, more preferably not less than 20% by weight, whereby sufficient adhesive force can be obtained.

The primer composition of the present invention can further contain an organic solvent (E) when the polymerizable monomer containing an acidic group (A) is difficult to dissolve in water. That is, it is also possible to use the primer composition after dissolving all the components using an organic solvent to prepare a homogeneous solution or an emulsion of such an extent that it does not cause a problem when in use.

Specific examples of the organic solvent include alcohols and ethers such as methanol, ethanol, propanol, isopropanol, butanol, isobutanol, propanediol, butanediol, pentanediol, hexanediol, butenediol, glycerine, trimethylolpropane, hexanetriol, allyl alcohol, ethylene glycol, ethylene glycol monomethyl ether, ethylene glycol monoethyl ether, diethylene glycol, diethylene glycol monomethyl ether, diethylene glycol monoethyl ether, triethylene glycol, triethylene glycol monomethyl ether, tetraethylene glycol, propylene glycol, dipropylene glycol, tripropylene glycol, 2-methoxyethanol, 2-ethoxyethanol, 2-(methoxyethoxy) ethanol, 2-isopropoxyethanol, 2-butoxyethanol, 1-methoxy-2-propanol, 1-ethoxy-2-propanol, dipropylene glycol, dipropylene glycol monomethyl ether, tripropylene glycol monomethyl ether and glycerine ether; ketones such as acetone and methyl ethyl ketone; carboxylic acids such as acetic acid, acetic anhydride and propionic acid; and the like. Solvents having a polymerizable functional group such as 2-hydroxyethyl (meth)acrylate, 2-hydroxypropyl (meth) acrylate, and N-methylol (meth)acryl amide may also be used.

Out of these, the preferred are solvents which are little harmful effect on vital function, such as ethanol, isopropanol, propanediol, butanediol, pentanediol, glycerine, trimethylolpropane, hexanetriol, aryl alcohol, ethylene glycol, ethylene glycol monomethyl ether, ethylene glycol monoethyl ether, ethylene glycol dimethyl ether, diethylene glycol, diethylene glycol monomethyl ether, diethylene glycol monoethyl ether, triethylene glycol, triethylene glycol monomethyl ether, tetraethylene glycol, propylene glycol, dipropylene glycol, tripropylene glycol, dipropylene glycol, dipropylene glycol monomethyl ether, tripropylene glycol monomethyl ether, glycerine ether, acetone, 2-hydroxyethyl methacrylate and the like.

The above organic solvents may be used in admixture of two or more as required.

In the primer composition containing the organic solvent (E) of the present invention, the weight proportions of the components (A), (C), (D) based on the total weight of the components (A), (B), (C), (D) and (E) are the same as the primer composition comprising the components (A), (B), (C) and (D), and the proportion of the organic solvent as the component (E) is 1 to 80% by weight and the water (B) occupies the remainder.

The primer composition of the present invention may contain other polymerizable monomer, water-insoluble organic solvent, polymerization catalyst other than aryl borates, polymerization inhibitor, pigment, inorganic and organic fillers in amounts that do not impair performance thereof.

Examples of the other polymerizable monomer include monofunctional polymerizable monomers such as methyl methacrylate, ethyl methacrylate, tetrahydrofurfuryl methacrylate, 2-hydroxyethyl methacrylate, N-methylolmethacrylamide and acrylates thereof; aromatic difunctional monomers such as 2,2-bis(4-methacryloyloxyphenyl)propane, 2,2-bis(4-(2-hydroxy-3-methacryloyloxypropoxy)phenyl)propane, 2,2-bis(4-methacryloyloxyethoxyphenyl)propane, 2,2-bis(4-methacryloyloxydiethoxyphenyl)propane, 2,2-bis(4-methacryloyloxytetraethoxydiphenyl)propane, 2,2-bis(4-methacryloyloxypentaethoxyphenyl)propane, 2,2-bis(4-methacryloyloxydipropoxyphenyl)propane, 2(4-methacryloyloxyethoxy)phenyl-2-(4-methacryloyloxydiethoxyphenyl)propane, 2(4-methacryloyloxydiethoxyphenyl)-4-methacryloyloxytriethoxyphenyl)propane, 2(4-methacryloyloxydipropoxyphenyl)propane, 2,2-bis(4-methacryloyloxyisopropoxyphenyl)propane, and acrylates corresponding thereto; aliphatic difunctional monomers such as ethylene glycol dimethacrylate, diethylene glycol dimethacrylate, triethylene glycol dimethacrylate, butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate, and acrylates corresponding to these; trifunctional monomers such as trimethylol propane trimethacrylate, trimethylolethane trimethacrylate, trimethylolpropane trimethacrylate, and acrylates corresponding to these; tetrafunctional monomers such as pentaerythritol tetramethacrylate and pentaerythritol tetraacrylate; and the like.

Examples of the water-insoluble organic solvent include hexane, butane, octane, toluene, dichloromethane, chloroform, carbon tetrachlordie, dichloromethane, trichloroethane, methyl ethyl ketone, pentanone, ethyl formate, propyl formate, butyl formate, ethyl acetate, propyl acetate, butyl acetate and the like.

Examples of the polymerization catalyst other than aryl borates include organic peroxides such as d-t-butyl peroxide, dicumyl peroxide, lauroyl peroxide and benzoyl peroxide; azo compounds such as azobisisobutyronitrile; sulfinic acid salts such as sodium benzenesulfinate, sodium p-toluenesulfinate, sodium m-nirobenzenesulfinate and sodium p-fluorobenzenesulfinate; barbituric acids such as 5-butylbarbituric acid and 1-benzyl-5-phenylbarbituric acid; and the like. Examples of the polymerization catalyst which generates a radical with light include α-diketones such as camphorquinone, benzyl, α-naphthyl, acetonaphthene and naphthoquinone; thioxanthones such as 2,4-diethylthioxanthone and 2-chlorothioxanthone; and optical initiators such as 2-benzyl-dimethylamino-1-(4-morphilinophenyl)butanonone-1 and the like. Promoters for the above optical initiators include, for example, tertiary amines such as N,N-dimethylaniline, N,N-dimethylamino-p-toluidine, ethyl N,N-dimethylamino-p-benzoate, isoamyl N,N-dimethylamino-p-benzoate and N,N-dimethylamino-p-acetophenone; and amino acids such as N-phenylglycine.

As for the package of the dental primer of the present invention, the aryl borate is preferably packaged separately from the polymerizable monomer containing an acidic group and the transition metal compound because they are blended right before use. Since the aryl borate generates a radical under an acidic condition thereby to decompose, it need be packaged separately from the polymerizable monomer containing an acidic group as an acid component and the transition metal compound. For example, it is preferred that a solution containing the polymerizable monomer containing an acidic group, the transition metal compound and the organic solvent as main ingredients and a solution containing water and an aryl borate as main ingredients should be prepared, packaged separately and mixed together right before use.

As for bonding operation using the dental primer of the present invention, this primer is applied to the surface of a tooth using a sponge or brush, left for a few seconds to a few minutes and thereafter dried by air blowing. Then, an adhesive is applied to the pretreated surface of the tooth, various repair materials are brought into contact with the surface, and the adhesive is cured by polymerization to make the crown material to be firmly bonded to the tooth.

The dental primer of the present invention may be divided for use. For example, after the surface of a tooth is pretreated with an aqueous solution of the transition metal compound, it may be treated with an organic solution of the polymerizable monomer containing an acidic group and the aryl borate. In this case, it is considered that the primer composition of the present invention is formed on the surface of the tooth.

The aryl borate used in the primer composition of the present intention is useful as a catalyst for the polymerization of a polymerizable monomer when it is used in combination with the transition metal compound and the acidic compound. All the polymerizable monomers listed above are used as the polymerizable monomer. The acidic compound can be such a polymerizable monomer containing an acidic group as described above, but may be an inorganic acid such as hydrochloric acid, phosphoric acid, nitric acid or sulfuric acid; an organic acid such as citric acid, maleic acid, malonic acid, acetic acid, oxalic acid, butyric acid, succinic acid, fumaric acid, benzoic acid or benzenesulfonic acid; and further, an acidic compound such as a compound which is used as an optically cationic polymerization catalyst and generates an acid when it is exposed to light is also usable.

According to the present invention, there are also provided catalyst components for the polymerization of a polymerizable monomer, which comprise a combination of an aryl borate and a transition metal compound, such as catalyst components for polymerizing a dental composition comprising a polymerizable monomer, and a polymerization catalyst containing these polymerization catalyst components and an acidic compound, such as a polymerization catalyst for a dental composition comprising a monomer containing an acidic group.

The dental primer composition of the present invention can exhibit high adhesive strength to both dentin and enamel not only when an optically polymerizable adhesive is used but also when a chemically polymerizable adhesive is used in the bonding of a crown repair material to the tooth.

EXAMPLES

The following examples are given to further specifically illustrate the present invention. However, it is to be understood that the present invention is in no way limited by these examples. Compounds and their abbreviations used in the specification and examples are given below.

(1) Abbreviations and Structures

Phenyl-P: 2-methacryloyloxyethylphenyl hydrogen phosphate
PM: 2-methacryloyloxyethyl dihydrogen phosphate
PM-2: bis(2-methacryloyloxyethyl)hydrogen phosphate
MAC-10: 11-methacryloyloxy-1,1-undecanedicarboxylic acid
MTS: 2-methacryloyloxyethyl 3'-methacryloyloxy-2'-(3,4-dicarboxybenzoyloxy)propyl succinate
EGDME: ethylene glycol dimethyl ether
EGMEA: ethylene glycol monomethylether acetate
EGEEA: ethylene glycol monoethyl ether acetate
BPO: benzoyl peroxide
DMPT: N,N-dimethyl-p-toluidine
CQ: camphorquinone PBNa;

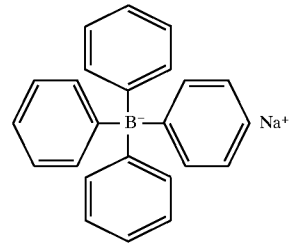

FPBNa;

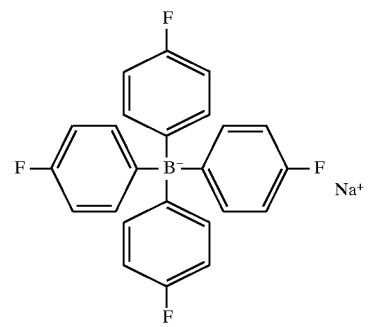

ClPBK;

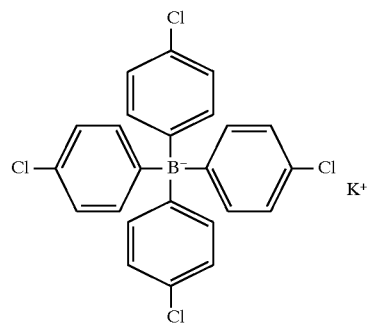

4p-MPBNa;

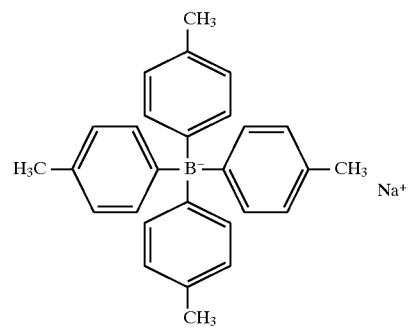

p-MEPBNa;

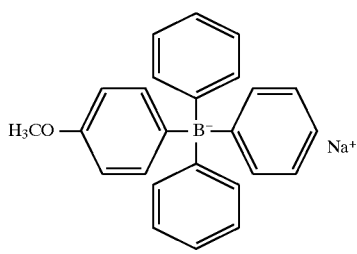

4m-MEPBNa;

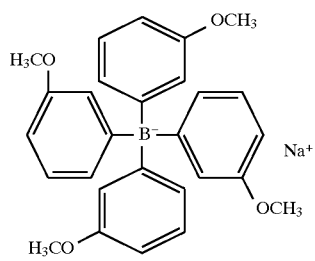

m-C4PBNa;

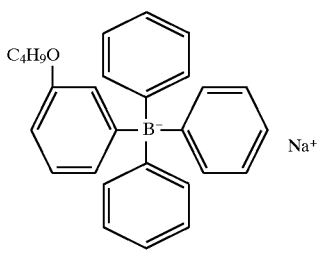

4m-C4PBNa;

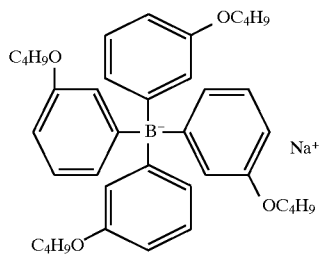

n-BPBNa;

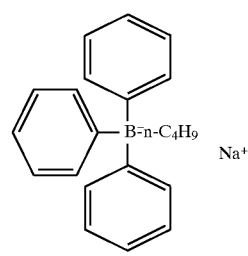

n-BPBMA;

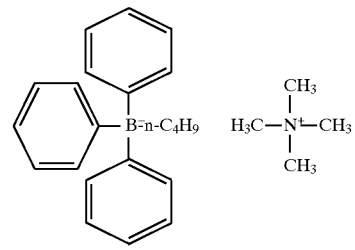

PBMP;

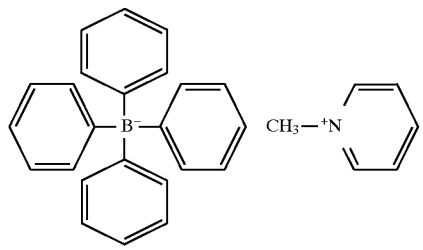

PBMA;

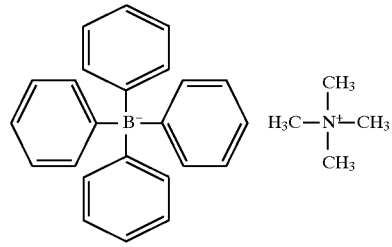

BPNa;

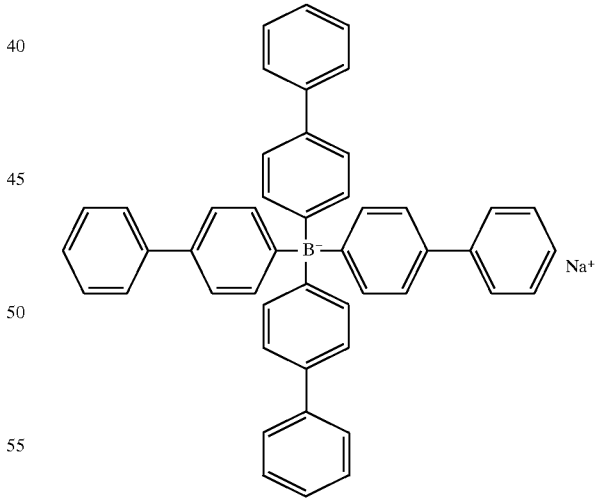

The aryl borate used in the present invention can be synthesized by a known method, but an example thereof is shown below.

Production Example 1

1.46 Grams (0.06 mol) of metal magnesium and 10 ml of tetrahydrofuran (THF) dried in advance were charged in a 300 ml three-necked flask, and stirred at room temperature for 30 minutes in a nitrogen atmosphere. To this solution was added small amounts of iodine and 1,2-dibromoethane dropwise. Thereafter, 9.352 g (0.05 mol) of 3-bromoanisole was added dropwise to the resulting mixture slowly using a dropping funnel under cooling with ice. After dropping, the mixture was refluxed for 1 hour and then, it was left to stand until its temperature became room temperature. To this reaction solution was dropwise added 1.70 g (0.012 mol) of a trifluoroborane diethyl ether complex and then, refluxed for 1 hour. After having left it stand, 200 ml of an aqueous solution containing 18 g (0.45 mol) of sodium hydroxide was added thereto. After stirring the solution at room temperature for 1 hour, sodium chloride was added to the reaction solution for saturation to separate a water layer. The separated water layer was extracted twice using 150 ml of THF. After an organic layer was dried over sodium sulfate, the solvent was distilled off under a reduced pressure. The obtained solid was recrystallized from hexane to give 3.60 g of a white solid which was an object product of tetrakis (m-methoxyphenyl)borate sodium. The result of NMR ($d_6$DMSO) analysis is shown below.

NMR (δ, ppm): 3.6 (3H, —OCH$_3$), 6.4 (1H, a), 6.7 (1H, b, c), 6.8 (1H, d).

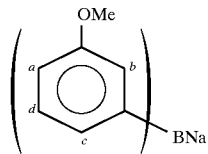

The adhesive strength was evaluated in accordance with the following test method.

(2) Measurement Method of Adhesive Strength

Pretreatment Method

A bovine front tooth was removed within 24 hours after slaughter and the surface of the enamel or dentin was abraded to expose with #800 Emery paper under injection of water so as to become flush with the surface of a lip. Thereafter, the surface was dried by a blow of compressed air for about 10 seconds, and a double-sided adhesive tape having a 4 mm-diameter hole was fixed to this flat surface to define an adhesion area. The dental primer of concern was applied thinly to this area, left for 30 seconds and dried by a blow of compressed air for about 10 seconds.

Bonding with an Optically Curable Adhesive

The MACBOND bonding material (a product of Tokuyama Corporation.) which was an optically curable adhesive was applied to the adhesion surface prepared by the above method, and cured by irradiation using a POWER LIGHT (a product of Tokuyama Corporation.) for 10 seconds. Thereafter, a 4 mm-thick wax having a 6 mm-diameter hole was adhered to the double-sided tape concentrically to prepare a mimic cavity. The PALFIQUE LITEPOSTERIOR (a product of Tokuyama Corporation.), which was a photo-curable composite resin, was filled into this mimic cavity. The mimic cavity was covered by a polypropylene sheet and irradiated with light for 30 seconds to polymerize to cure the composite resin to prepare a test sample. This test sample was immersed in water at 37° C. for 24 hours and thereafter, subjected to a tensile test at a cross head speed of 10 mm/min using a tensile testor (AUTOGRAPH supplied by Shimadzu Corp.).

Bonding with a Chemically Curable Adhesive

The BISTITE RESIN CEMENT (a product of Tokuyama Corporation.) which was prepared by kneading two different pastes on a mixing pad for 10 seconds to obtain an uniform mixture was applied to the pretreated adhesion area and an 8 mm-diameter stainless steel attachment was contacted under pressure to the cement to prepare a test sample. This test sample was kept at 37° C. in a humid atmosphere for 1 hour, immersed in water at 37° C. for 24 hours and then, measured for its tensile adhesive strength at a cross head speed of 10 mm/min using a tensile tester (Autograph AG5000 of Shimadzu Corp.).

Four adhesion test samples were measured for each test and an average value of the measurement values was taken as adhesive strength.

Example 1

A solution A consisting of 0.5 g of Phenyl-P, 1.5 g of PM and 10 mg of copper (II) citrate (½) hydrate and a solution B consisting of 0.3 g of PBNa and 7.7 g of water were mixed together right before use to prepare an uniform suspension. This suspension was used as a primer to treat the surface of a tooth, and bonding operation was carried out using the BISTITE RESIN CEMENT. Adhesive strength when a chemically polymerizable adhesive was used was measured. The results are shown in Table 1. The adhesive strength to the dentin was 10.5 MPa and the adhesive strength to the enamel was 17.2 MPa.

Example 2

A solution A consisting of 1.5 g of Phenyl-P, 1.0 g of MTS, 10 mg of copper (II) citrate (½) hydrate and 1.5 g of EGDME and a solution B consisting of 5.7 g of water and 0.3 g of PBNa were mixed together right before use. The resulting solution was used as a primer to treat the surface of a tooth, bonding operation was carried out using the BISTITE RESIN CEMENT, and the adhesive strength was measured. The results are shown in Table 1. The adhesive strength to the dentin was 12.9 MPa and the adhesive strength to the enamel was 18.3 MPa.

Examples 3 to 35

Primers were prepared in the same manner as in Example 2, and bonding operation was carried out using the BISTITE RESIN CEMENT. The compositions of the primers and the adhesive strengths to the dentin are shown in Tables 1 to 4. Examples 3 to 10 are cases where the kind and amount of the polymerizable monomer containing an acidic group contained in the primers used were changed. Examples 11 to 17 are cases where the kind and amount of the transition metal compound were changed and Examples 18 to 21 are cases where the kind of the organic solvent was changed. Examples 22 to 33 are cases where the kind and amount of the aryl borate were changed and Examples 34 and 35 cases where the amount of water was changed. In all the cases, excellent adhesive strength was obtained.

TABLE 1

| Ex. No. | (A) polymerizable monomer containing acidic group | | (D) transition metal compound | | (E) organic solvent | | (C) aryl borate | | (B) water | Adhesive strength to dentin (MPa) | Adhesive strength to enamel (MPa) |
|---|---|---|---|---|---|---|---|---|---|---|---|
| 1 | Phenyl-P<br>PM | 5<br>15 | Copper citrate | 0.1 | — | | PBNa | 3 | 77 | 10.5 | 17.2 |
| 2 | Phenyl-P<br>MTS | 15<br>10 | Copper citrate | 0.1 | EGDME | 15 | PBNa | 3 | 57 | 12.9 | 18.3 |
| 3 | Phenyl-P<br>MAC-10 | 5<br>4 | Copper citrate | 0.1 | EGDME | 31 | PBNa | 3 | 57 | 13.4 | 17.8 |
| 4 | Phenyl-P | 15 | Copper citrate | 0.1 | EGDME | 25 | PBNa | 3 | 57 | 10.3 | 16.7 |
| 5 | PM-2<br>MTS | 10<br>10 | Copper citrate | 0.1 | EGDME | 20 | PBNa | 3 | 57 | 10.8 | 16.6 |
| 6 | PM-2<br>PM<br>MAC-10 | 9<br>6<br>5 | Copper citrate | 0.1 | EGDME | 25 | PBNa | 3 | 57 | 12.3 | 19.9 |
| 7 | PM-2<br>PM<br>MTS | 9<br>6<br>10 | Copper citrate | 0.1 | EGDME | 15 | PBNa | 3 | 57 | 11.4 | 18.2 |
| 8 | PM-2<br>PM | 10.8<br>7.2 | Copper citrate | 0.1 | EGDME | 22 | PBNa | 3 | 57 | 10.0 | 17.2 |

Ex.: Example

TABLE 2

| Ex. No. | (A) polymerizable monomer containing acidic group | | (D) transition metal compound | | (E) organic solvent | | (C) aryl borate | | (B) water | Adhesive strength to dentin (MPa) | Adhesive strength to enamel (MPa) |
|---|---|---|---|---|---|---|---|---|---|---|---|
| 9 | Phenyl-P<br>MTS | 10<br>10 | Copper acetate | 0.1 | EGDME | 20 | PBNa | 1 | 59 | 12.0 | 20.6 |
| 10 | Phenyl-P<br>MAC-10 | 10<br>8 | Copper (II) chloride | 0.1 | EGDME | 22 | PBNa | 1 | 59 | 10.6 | 17.3 |
| 11 | Phenyl-P<br>MTS | 15<br>10 | Cobalt acetyl acetate | 0.1 | EGDME | 15 | PBNa | 3 | 57 | 10.7 | 18.4 |
| 12 | Phenyl-P<br>MAC-10 | 10<br>8 | Iron acetyl acetate | 0.1 | EGDME | 22 | PBNa | 3 | 57 | 12.3 | 18.0 |
| 13 | PM-2<br>PM | 10.8<br>7.2 | Iron (III) chloride | 0.4 | EGDME | 21.6 | PBNa | 3 | 57 | 10.1 | 17.2 |
| 14 | Phenyl-P<br>MTS | 15<br>10 | Copper citrate | 0.02 | EGDME | 20 | PBNa | 2 | 53 | 10.9 | 17.1 |
| 15 | Phenyl-P<br>MTS | 10<br>12 | Copper citrate | 0.5 | EGDME | 22.5 | PBNa | 2 | 53 | 11.2 | 19.1 |
| 16 | PM-2<br>PM | 9<br>6 | Iron (III) chloride | 1.0 | EGDME | 28 | PBNa | 3 | 53 | 10.5 | 20.2 |
| 17 | PM-2<br>PM | 9<br>6 | Copper (III) chloride | 3.0 | EGDME | 26 | PBNa | 3 | 53 | 10.3 | 18.2 |

Ex.: Example

TABLE 3

| Ex. No. | (A) polymerizable monomer containing acidic group | | (D) transition metal compound | | (E) organic solvent | | (C) aryl borate | | (B) water | Adhesive strength to dentin (MPa) | Adhesive strength to enamel (MPa) |
|---|---|---|---|---|---|---|---|---|---|---|---|
| 18 | Phenyl-P<br>MTS | 15<br>10 | Copper citrate | 0.1 | EGMEA | 19 | PBNa | 3 | 53 | 12.2 | 16.3 |
| 19 | Phenyl-P<br>MTS | 15<br>10 | Copper citrate | 0.1 | EGEEA | 19 | PBNa | 3 | 53 | 10.3 | 16.4 |

TABLE 3-continued

| Ex. No. | (A) polymerizable monomer containing acidic group | | (D) transition metal compound | | (E) organic solvent | | (C) aryl borate | | (B) water | Adhesive strength to dentin (MPa) | Adhesive strength to enamel (MPa) |
|---|---|---|---|---|---|---|---|---|---|---|---|
| 20 | PM-2 PM MTS | 9 6 10 | Copper citrate | 0.1 | EGDMA Acetone | 9 10 | PBNa | | 3 | 53 | 11.0 | 17.7 |
| 21 | PM-2 PM MAC-10 | 9 6 10 | Iron acetyl acetate | 0.1 | Acetone | 19 | PBNa | | 3 | 53 | 10.8 | 18.6 |
| 22 | Phenyl-P MTS | 15 10 | Copper citrate | 1.0 | EGDME | 14 | FPBNa | | 3 | 57 | 11.5 | 17.4 |
| 23 | Phenyl-P MTS | 15 10 | Copper citrate | 0.1 | EGDME | 15 | CIPBK | | 3 | 57 | 10.7 | 18.4 |
| 24 | Phenyl-P MTS | 15 10 | Copper citrate | 0.1 | EGDME | 34 | 4p-MPBNa | | 1 | 40 | 12.6 | 18.8 |
| 25 | Phenyl-P MAC-10 | 15 10 | Copper citrate | 0.1 | EGDME | 17 | p-MEPBNa | | 1 | 57 | 12.5 | 19.3 |
| 26 | PM-2 PM | 10.2 7.8 | Iron (III) chloride | 3.0 | EGDME Acetone | 18 20 | 4m-MEPBNa | | 3 | 38 | 12.0 | 19.5 |

Ex.: Example

TABLE 4

| Ex. No. | (A) polymerizable monomer containing acidic group | | (D) transition metal compound | | (E) organic solvent | | (C) aryl borate | | (B) water | Adhesive strength to dentin (MPa) | Adhesive strength to enamel (MPa) |
|---|---|---|---|---|---|---|---|---|---|---|---|
| 27 | PM-2 PM | 10.2 7.8 | Iron (III) chloride | 0.6 | EGDMA Acetone | 20 11.4 | m-C4PBNa | | 3 | 47 | 11.0 | 18.8 |
| 28 | Phenyl-P MTS | 15 5 | Copper acetate | 0.1 | EGEEA Acetone | 20 10 | 4m-C4PBNa | | 10 | 35 | 11.7 | 16.1 |
| 29 | PM-2 PM MTS | 9 6 10 | Copper citrate | 0.1 | EGDMA | 18.0 | n-BPBNa | | 2 | 55 | 13.6 | 20.3 |
| 30 | PM-2 PM MAC-10 | 9 6 7 | Copper citrate | 0.1 | Acetone | 21 | n-BPBNa | | 2 | 55 | 12.2 | 20.7 |
| 31 | Phenyl-P MTS | 15 10 | Copper citrate | 0.1 | EGDMA Acetone | 20 17 | BPBNa | | 3 | 35 | 10.3 | 18.2 |
| 32 | Phenyl-P MAC-10 | 15 10 | Copper citrate | 0.5 | EGDME | 29.5 | PBMP | | 1 | 45 | 10.3 | 16.5 |
| 33 | Phenyl-P MTS | 15 10 | Copper acetate | 0.1 | EGDME | 35 | PBMA | | 1 | 39 | 10.9 | 18.0 |
| 34 | Phenyl-P MTS | 15 10 | Copper citrate | 0.5 | EGDME Acetone | 30 18.5 | PBNa | | 1 | 25 | 10.3 | 16.5 |
| 35 | Phenyl-P MAC-10 | 10 10 | Copper acetate | 0.05 | EGDME | 20 | PBNa | | 3 | 67 | 11.2 | 18.6 |

Ex.: Example

Comparative Examples 1 to 8

Primers were prepared in the same manner as in Example 2, and the adhesive strength to the dentin was evaluated using the BISTITE RESIN CEMENT. The compositions of the primers and the results are shown in Table 5.

In contrast to the above Examples, Comparative Examples 1 to 4 are cases where one of the aryl borate, transition metal compound, polymerizable monomer containing an acidic group and water as essential components of the present invention lacked, and in all the cases, the adhesive strengths to both dentin and enamel degraded. Comparative Examples 4 and 5 are cases where the constitution proportion of the essential components was outside the range of the present invention, and in all these cases, the adhesive strength to dentin or enamel lowered. Comparative Examples 6 to 9 are cases where other polymerization initiator and/or a promoter were/was used in place of the aryl borate and the adhesive strengths to both dentin and enamel deteriorated in all the cases.

TABLE 5

| Comp. Ex. No. | (A) polymerizable monomer containing acidic group | | (D) transition metal compound | | (E) organic solvent | | (C) aryl borate | | (B) water | Adhesive strength to dentin (MPa) | Adhesive strength to enamel (MPa) |
|---|---|---|---|---|---|---|---|---|---|---|---|
| 1 | Phenyl-P<br>MTS | 15<br>10 | Copper citrate | 0.1 | EGDME | 15 | — | | 60 | 0 | 4.2 |
| 2 | Phenyl-P<br>MTS | 15<br>10 | — | | EGDME | 15 | PBNa | 1 | 35 | 5.0 | 10.2 |
| 3 | — | | Copper citrate | 0.1 | EGDME | 40 | PBNa | 3 | 55 | 2.1 | 3.5 |
| 4 | Phenyl-P<br>MTS | 15<br>10 | Copper citrate | 0.1 | EGDME | | PBNa | 1 | — | 6.6 | 5.4 |
| 5 | PM<br>MAC-10 | 35<br>25 | Copper citrate | 0.1 | EGDME | | PBNa | 1 | 5 | 3.6 | 4.7 |
| 6 | Phenyl-P<br>MTS | 10<br>10 | Copper citrate | 0.1 | EGDME | 17 | Other catalyst BPO | 3 | 55 | 0 | 7.8 |
| 7 | Phenyl-P<br>MTS | 10<br>10 | Copper citrate | 0.1 | EGDME | 30 | Other catalyst DMPT | 3 | 40 | 1.0 | 8.0 |
| 8 | Phenyl-P<br>MTS | 10<br>10 | Copper citrate | 0.1 | EGDME | 40 | Other catalyst BPO DMPT | 3<br>3 | 39 | 1.2 | 9.7 |
| 9 | Phenyl-P<br>MTS | 15<br>10 | Copper citrate | 0.1 | EGDME | 25 | PTsNa | 3 | 47 | 7.1 | 17.8 |

Comp. Ex.: Comparative Example

Example 36

In the same manner as in Example 1, a solution A consisting of 0.5 g of Phenyl-P, 1.5 g of PM and 10 mg of copper (II) citrate (½) hydrate and a solution B consisting of 0.3 g of PBNa and 7.7 g of water were mixed together right before use to prepare an uniform suspension. The suspension was used as a primer to treat the surface of a tooth, bonding operation was carried out using the MACBOND, and the adhesive strength when an optically curable adhesive was used was measured. The results are shown in Table 6. The adhesive strength to the dentin was 15.2 MPa and the adhesive strength to the enamel was 20.3 MPa.

Examples 37 to 70

Primers were prepared in the same manner as in Examples 2 to 35, and bonding operation was carried out using the MACBOND in place of the BISTITE RESIN CEMENT which is a chemically curable adhesive. The adhesive strengths when an optically curable adhesive was used were measured. The primer compositions and results are shown in Tables 6 to 9.

Excellent adhesive strengths to both dentin and enamel were obtained in all the examples.

TABLE 6

| Ex. No. | (A) polymerizable monomer containing acidic group | | (D) transition metal compound | | (E) organic solvent | | (C) aryl borate | | (B) water | Adhesive strength to dentin (MPa) | Adhesive strength to enamel (MPa) |
|---|---|---|---|---|---|---|---|---|---|---|---|
| 36 | Phenyl-P<br>PM | 5<br>15 | Copper citrate | 0.1 | — | | PBNa | 3 | 77 | 15.2 | 20.3 |
| 37 | Phenyl-P<br>MTS | 15<br>10 | Copper citrate | 0.1 | EGDME | 15 | PBNa | 3 | 57 | 20.7 | 23.1 |
| 38 | Phenyl-P<br>MAC-10 | 5<br>4 | Copper citrate | 0.1 | EGDME | 31 | PBNa | 3 | 57 | 19.8 | 22.8 |
| 39 | Phenyl-P | 15 | Copper citrate | 0.1 | EGDME | 25 | PBNa | 3 | 57 | 17.6 | 20.9 |
| 40 | PM-2<br>MTS | 1.0<br>10 | Copper citrate | 0.1 | EGDME | 20 | PBNa | 3 | 57 | 19.9 | 20.6 |
| 41 | PM-2<br>PM<br>MAC-10 | 9<br>6<br>5 | Copper citrate | 0.1 | EGDME | 25 | PBNa | 3 | 57 | 20.4 | 21.0 |
| 42 | PM-2<br>PM<br>MTS | 9<br>6<br>10 | Copper citrate | 0.1 | EGDME | 15 | PBNa | 3 | 57 | 18.7 | 22.3 |
| 43 | PM-2<br>PM | 10.8<br>7.2 | Copper citrate | 0.1 | EGDME | 22 | PBNa | 3 | 57 | 16.3 | 20.7 |

Ex.: Example

TABLE 7

| Ex. No. | (A) polymerizable monomer containing acidic group | | (D) transition metal compound | | (E) organic solvent | | (C) aryl borate | | (B) water | Adhesive strength to dentin (MPa) | Adhesive strength to enamel (MPa) |
|---|---|---|---|---|---|---|---|---|---|---|---|
| 44 | Phenyl-P MTS | 10 10 | Copper acetate | 0.1 | EGDME | 20 | PBNa | 1 | 59 | 21.3 | 22.4 |
| 45 | Phenyl-P MAC-10 | 10 8 | Copper (II) chloride | 0.1 | EGDME | 22 | PBNa | 1 | 59 | 18.1 | 21.6 |
| 46 | Phenyl-P MTS | 15 10 | Cobalt acetyl acetate | 0.1 | EGDME | 15 | PBNa | 3 | 57 | 17.5 | 23.1 |
| 47 | Phenyl-P MAC-10 | 10 8 | Iron acetyl acetate | 0.1 | EGDME | 22 | PBNa | 3 | 57 | 19.2 | 21.9 |
| 48 | PM-2 PM | 10.8 7.2 | Iron (III) chloride | 0.4 | EGDME | 21.6 | PBNa | 3 | 57 | 16.6 | 21.6 |
| 49 | Phenyl-P MTS | 15 10 | Copper citrate | 0.02 | EGDME | 20 | PBNa | 2 | 53 | 15.8 | 18.8 |
| 50 | Phenyl-P MTS | 10 12 | Copper citrate | 0.5 | EGDME | 22.5 | PBNa | 2 | 53 | 19.6 | 20.1 |
| 51 | PM-2 PM | 9 6 | Iron (III) chloride | 1.0 | EGDME | 28 | PBNa | 3 | 53 | 18.7 | 22.7 |
| 52 | PM-2 PM | 9 6 | Copper (III) chloride | 3.0 | EGDME | 26 | PBNa | 3 | 53 | 17.6 | 20.4 |

Ex.: Example

TABLE 8

| Ex. No. | (A) polymerizable monomer containing acidic group | | (D) transition metal compound | | (E) organic solvent | | (C) aryl borate | | (B) water | Adhesive strength to dentin (MPa) | Adhesive strength to enamel (MPa) |
|---|---|---|---|---|---|---|---|---|---|---|---|
| 53 | Phenyl-P MTS | 15 10 | Copper citrate | 0.1 | EGMEA | 19 | PBNa | 3 | 53 | 20.6 | 20.4 |
| 54 | Phenyl-P MTS | 15 10 | Copper citrate | 0.1 | EGEEA | 19 | PBNa | 3 | 53 | 19.5 | 21.3 |
| 55 | PM-2 PM MTS | 9 6 10 | Copper citrate | 0.1 | EGDMA Acetone | 9 10 | PBNa | 3 | 53 | 20.7 | 22.6 |
| 56 | PM-2 PM MAC-10 | 9 6 10 | Iron acetyl acetate | 0.1 | Acetone | 19 | PBNa | 3 | 53 | 20.0 | 21.1 |
| 57 | Phenyl-P MTS | 15 10 | Copper citrate | 1.0 | EGDME | 14 | FPBNa | 3 | 57 | 17.6 | 19.4 |
| 58 | Phenyl-P MTS | 15 10 | Copper citrate | 0.1 | EGDME | 15 | ClPBK | 3 | 57 | 18.3 | 20.8 |
| 59 | Phenyl-P MTS | 15 10 | Copper citrate | 0.1 | EGDME | 34 | 4p-MPBNa | 1 | 40 | 20.3 | 22.7 |
| 60 | Phenyl-P MAC-10 | 15 10 | Copper citrate | 0.1 | EGDME | 17 | p-MEPBNa | 1 | 57 | 21.3 | 21.0 |
| 61 | PM-2 PM | 10.2 7.8 | Iron (III) chloride | 3.0 | EGDME Acetone | 18 20 | 4m-MEPBNa | 3 | 38 | 20.6 | 22.5 |

Ex.: Example

TABLE 9

| | Primer composition (parts by weight) | | | | | | | | | | Adhesive strength to dentin (MPa) | Adhesive strength to enamel (MPa) |
|---|---|---|---|---|---|---|---|---|---|---|---|---|
| Ex. No. | (A) polymerizable monomer containing acidic group | | (D) transition metal compound | | (E) organic solvent | | (C) aryl borate | | (B) water | | | |
| 62 | PM-2<br>PM | 10.2<br>7.8 | Iron (III) chloride | 0.6 | EGDMA<br>Acetone | 20<br>13.4 | m-C4PBNa | | 1 | 47 | 21.6 | 23.0 |
| 63 | Phenyl-P<br>MTS | 15<br>10 | Copper acetate | 0.1 | EGEEA<br>Acetone | 20 | 4m-C4PBNa | | 1 | 35 | 20.5 | 22.6 |
| 64 | PM-2<br>PM<br>MTS | 9<br>6<br>10 | Copper citrate | 0.1 | EGDMA | 19.9 | PBBNa | | 1 | 55 | 21.2 | 22.4 |
| 65 | PM-2<br>PM<br>MAC-10 | 9<br>6<br>7 | Iron (III) chloride | 0.4 | Acetone | 21.6 | BPBNa | | 1 | 55 | 19.2 | 21.2 |
| 66 | Phenyl-P<br>MTS | 15<br>10 | Copper citrate | 1.0 | EGDME | 17 | BPBB | | 3 | 55 | 17.8 | 22.3 |
| 67 | Phenyl-P<br>MAC-10 | 15<br>10 | Copper citrate | 0.5 | EGDME<br>Acetone | 30<br>18.5 | m-BPBNa | | 1 | 25 | 20.2 | 21.4 |
| 68 | Phenyl-P<br>MTS | 15<br>10 | Copper acetate | 0.1 | EGDME | 40 | PBNa | | 1 | 39 | 17.3 | 20.1 |
| 69 | Phenyl-P<br>MTS | 15<br>10 | Copper citrate | 0.05 | EGDME | 25 | PBNa | | 3 | 47 | 18.6 | 19.2 |
| 70 | Phenyl-P<br>MAC-10 | 10<br>10 | Copper acetate | 0.05 | EGDME | 20 | PBNa | | 3 | 67 | 20.5 | 23.3 |

Ex.: Example

We claim:

1. A dental primer composition comprising:
(A) a polymerizable monomer containing an acidic group,
(B) water,
(C) an aryl borate represented by the following formula (1):

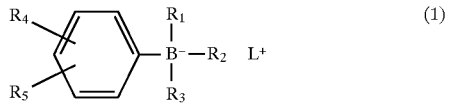

wherein $R_1$, $R_2$ and $R_3$ are the same or different and each is an alkyl group, alkenyl group, alkinyl group, aryl group, aralkyl group or alkaryl group and may be substituted, $R_4$ and $R_5$ are the same or different and each is a hydrogen atom, halogen atom, alkyl group which may be substituted or aryl group which may be substituted, and $L^+$ is a metal ion, quaternary ammonium salt, quaternary pyridinium salt, quaternary quinolinium ion or phosphonium ion, and
(D) a transition metal compound.

2. The primer composition of claim 1 which comprises 5 to 55% by weight of the polymerizable monomer containing an acidic group (A), 0.1 to 20% by weight of the aryl borate (C), 0.0001 to 20% by weight of the transition metal compound (D) and the remainder being water (B), based on the total of the components (A), (B), (C) and (D).

3. The primer composition of claim 1, wherein the polymerizable monomer containing an acidic group (A) is a polymerizable monomer containing an acidic group selected from the group consisting of a carboxylic acid group, phosphoric acid group, sulfonic acid group and phosphonic acid group.

4. The primer composition of claim 1, wherein the polymerizable monomer containing an acidic group (A) is a polymerizable monomer containing at least one polymerizable group selected from the group consisting of an acryloyl group, methacryloyl group, styryl group, vinyl group and allyl group.

5. The primer composition of claim 1, wherein the transition metal compound (D) is a halide, organic acid salt, inorganic acid salt or organic complex of a transition metal.

6. The primer composition of claim 5, wherein the transition metal is cobalt or copper.

7. A dental primer composition comprising (A) a polymerizable monomer containing an acidic group, (B). water, (C) an aryl borate, (D) a transition metal compound and (E) an organic solvent.

8. The primer composition of claim 7 which comprises 5 to 55% by weight of the polymerizable monomer containing an acidic group (A), 0.1 to 20% by weight of the aryl borate (C), 0.0001 to 20% by weight of the transition metal compound (D), 1 to 80% by weight of the organic solvent (E) and the remainder being water (B), based on the total of the components (A), (B), (C), (D) and (E).

9. The primer composition of claim 7, wherein the aryl borate (C) is kept separately from the polymerizable monomer containing an acidic group (A) and the transition metal compound (D) because they are blended before use.

10. The primer composition of claim 3, wherein the polymerizable monomer containing a carboxylic acid group is a monocarboxylic acid, dicarboxylic acid, tricarboxylic acid or tetracarboxylic acid.

11. The primer composition of claim 3, wherein the polymerizable monomer containing a phosphoric acid group is 2-(meth)acryloyloxyethyl dihydrogen phosphate, 2-(meth)acryloyloxyethyl acid phosphate, 2 or 3-(meth)acryloyloxypropyl acid phosphate, 4-(meth)acryloylbutyl acid phosphate, 6-(meth)acryloyloxybutyl acid phosphate, 8-(meth)acryloyloxydecyl acid phosphate, 10-(meth)acryloyloxydecyl acid phosphate, 12-(meth)acryloyloxydodecyl acid phosphate, bis(2-(meth)acryloyloxyethyl)acid phosphate, bis(2-(meth)

acryloyloxyethyl)hydrogen phosphate, 2-(meth)acryloyloxyethylphenyl acid phosphate (phenyl-P), or 2-(meth)acryloyoxyethyl-p-ethoxyphenyl acid phosphate.

12. The primer composition of claim 3, wherein the polymerizable monomer containing a sulfonic acid group is 2-sulfoethyl(meth)acrylate, 2-methyl-2-(meth)acrylamidepropanesulfonic acid, 2 or 1-sulfo-1 or 2-propyl (meth)acrylate, 1 or 3-sulfo-2-butyl (meth)acrylate, 3-bromo-2-sulfo-2-propyl (meth)acrylate, 3-methoxy-1-sulfo-2-propyl (meth)acrylate, 1,1-dimethyl-2-sulfoethyl (meth)acrylamide, or 3-methoxy-1-sulfo-2-propyl (meth)acrylate.

13. The primer composition of claim 1, wherein the transition metal compound is selected from the group consisting of compounds containing bromide, chloride, fluoride, sulfate, nitrate, inorganic acid salt, organic acid salt, hydroxide, and organic complexes with acetylacetone.

14. The primer composition of claim 1, wherein the polymerizable monomer containing an acidic group (A) is used in a proportion from 5 to 25% by weight.

15. The primer composition of claim 1, wherein the proportion of aryl borate (C) is 0.2 to 15% by weight.

16. The primer composition of claim 1, wherein the proportion of the transition metal compound (D) is 0.02 to 10% by weight.

17. The primer composition of claim 1, wherein the proportion of water (B) is not less than 5% by weight.

18. A dental primer composition comprising (A) a polymerizable monomer containing an acidic group, (B) water, (C) an aryl borate represented by the following formula (1):

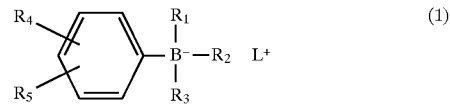

wherein $R_1$, $R_2$ and $R_3$ are the same or different and each is an alkyl group, alkenyl group, alkinyl group, aryl group, aralkyl group or alkaryl group and may be substituted, $R_4$ and $R_5$ are the same or different and each is a hydrogen atom, halogen atom, alkyl group which may be substituted or aryl group which may be substituted, and $L^+$ is a metal ion, quaternary ammonium salt, quartenary pyridinium salt, quaternary quinolinium ion or phosphonium ion, and (D) a transition metal compound and (E) an organic solvent.

19. A method for catalyzing a dental composition which comprises adding an aryl borate and a transition metal compound as a non-photopolymerization catalyst for said dental composition comprising a polymerizable monomer containing an acidic group and treating an oral dentin or enamel surface with said composition.

* * * * *